United States Patent
Mallard

(10) Patent No.: US 10,702,604 B2
(45) Date of Patent: Jul. 7, 2020

(54) LIPID NANOCAPSULES COMPRISING A RETINOID, NANODISPERSION AND COMPOSITION CONTAINING THE SAME, PROCESS FOR PREPARING THE SAME AND USE THEREOF IN DERMATOLOGY

(71) Applicant: GALDERMA RESEARCH & DEVELOPMENT, Biot (FR)

(72) Inventor: Claire Mallard, Mougins (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 94 days.

(21) Appl. No.: 14/404,901

(22) PCT Filed: May 30, 2013

(86) PCT No.: PCT/EP2013/061189
§ 371 (c)(1),
(2) Date: Dec. 1, 2014

(87) PCT Pub. No.: WO2013/178749
PCT Pub. Date: Dec. 5, 2013

(65) Prior Publication Data
US 2015/0125520 A1 May 7, 2015

Related U.S. Application Data

(60) Provisional application No. 61/654,718, filed on Jun. 1, 2012.

(30) Foreign Application Priority Data

Jun. 1, 2012 (FR) .................................. 12 55109

(51) Int. Cl.
| | | |
|---|---|---|
| A61K 9/51 | (2006.01) | |
| A61K 47/24 | (2006.01) | |
| A61K 47/14 | (2017.01) | |
| A61K 31/402 | (2006.01) | |
| A61K 9/00 | (2006.01) | |
| A61K 9/107 | (2006.01) | |
| A61K 31/203 | (2006.01) | |
| A61K 9/06 | (2006.01) | |
| A61K 9/48 | (2006.01) | |

(52) U.S. Cl.
CPC ............ *A61K 47/24* (2013.01); *A61K 9/0014* (2013.01); *A61K 9/06* (2013.01); *A61K 9/107* (2013.01); *A61K 9/1075* (2013.01); *A61K 9/4816* (2013.01); *A61K 31/203* (2013.01); *A61K 31/402* (2013.01); *A61K 47/14* (2013.01)

(58) Field of Classification Search
CPC .... A61K 9/1075; A61K 9/127; A61K 31/203; A61K 9/51; A61K 47/24
See application file for complete search history.

(56) References Cited

U.S. PATENT DOCUMENTS

| | | | |
|---|---|---|---|
| 5,100,591 A | 3/1992 | Leclef et al. | |
| 5,227,165 A | 7/1993 | Domb et al. | |
| 6,017,549 A | 1/2000 | Knight et al. | |
| 7,781,489 B2 * | 8/2010 | Menegatti | A61K 9/0014 514/725 |
| 7,807,708 B2 | 10/2010 | Biadatti et al. | |
| 8,057,823 B2 * | 11/2011 | Heurtault | A61K 9/5123 424/450 |
| 8,110,284 B2 | 2/2012 | Naigertsik et al. | |
| 8,309,121 B2 | 11/2012 | Baudonnet et al. | |
| 2005/0048088 A1 | 3/2005 | Zulli et al. | |
| 2007/0134276 A1 | 6/2007 | Menegatti et al. | |
| 2007/0184076 A1 | 8/2007 | Unger et al. | |
| 2008/0167375 A1 * | 7/2008 | Weidner | A61K 31/23 514/552 |
| 2008/0193393 A1 | 8/2008 | Dayan | |
| 2009/0258065 A1 | 10/2009 | Baudonnet et al. | |
| 2010/0098752 A1 | 4/2010 | Pinsky | |
| 2011/0195030 A1 * | 8/2011 | Mumper | A61K 9/1075 424/9.32 |
| 2015/0125520 A1 | 5/2015 | Mallard | |
| 2016/0310439 A1 | 10/2016 | Mallard et al. | |

FOREIGN PATENT DOCUMENTS

| | | |
|---|---|---|
| FR | 2805761 A1 | 9/2001 |
| WO | WO-91/07171 A1 | 5/1991 |
| WO | 2006/066978 A1 | 6/2006 |
| WO | WO-2010/113111 A1 | 10/2010 |
| WO | WO-2011/036234 A1 | 3/2011 |

OTHER PUBLICATIONS

English Translation of International Search Report dated Aug. 9, 2013 corresponding to International Patent Application No. PCT/EP2013/061189, 3 pages.
Liu et al. "Isotretinoin-loaded solid lipid nanoparticles with skin targeting for topical delivery." International journal of pharmaceutics 328.2 (2007): 191-195.

* cited by examiner

*Primary Examiner* — Lakshmi S Channavajjala
(74) *Attorney, Agent, or Firm* — Foley & Lardner LLP; Sunit Talapatra

(57) ABSTRACT

Lipid nanocapsules are described that include at least one irritating active ingredient, and more specifically a retinoid in solubilized form. Also described, are nanodispersions and pharmaceutical compositions including the same and methods of producing the same. The use of the pharmaceutical compositions in the treatment of dermatological pathologies is also described.

27 Claims, No Drawings

LIPID NANOCAPSULES COMPRISING A RETINOID, NANODISPERSION AND COMPOSITION CONTAINING THE SAME, PROCESS FOR PREPARING THE SAME AND USE THEREOF IN DERMATOLOGY

CROSS-REFERENCE TO PRIOR APPLICATIONS

This application is a National Stage of PCT/EP2013/061189, filed May 30, 2013, and designating the United States (published Dec. 5, 2013, as WO 2013/178749 A1), which claims priority under 35 U.S.C. § 119 to U.S. Provisional Application No. 61/654,718, filed Jun. 1, 2012, and French Patent Application No. 1255109, filed Jun. 1, 2012, each hereby expressly incorporated by reference in its entirety and each assigned to the assignee hereof.

The present invention relates to nanocapsules comprising an irritant active principle and more particularly a retinoid compound, said irritant active principle being present in dissolved form in the oil-based nanocapsules. The invention also relates to a nanodispersion composed of oil-based nanocapsules dispersed in an aqueous phase and to a pharmaceutical composition comprising the nanodispersion in a pharmaceutically acceptable vehicle. The invention also relates to a process for preparing the same and to the use of the pharmaceutical composition for treating dermatological complaints, in particular acne.

A person skilled in the art knows that the activity of certain pharmaceutical active principles is inseparable from a certain level of irritation. It is, however, essential to find compositions for maintaining the biological activity of the active principle while at the same time minimizing its irritant nature. Retinoids are active agents commonly used in dermatology, but the majority are known as being irritant active principles. It is therefore important, while maintaining the pharmaceutical activity, to improve the tolerance of this family of antiacne molecules.

The prior art discloses several formulation patents for improving the topical tolerance of retinoids, by adding anti-irritant compounds to the composition.

The Applicant has protected in patent FR 2 894 820 galenical formulations using anti-irritants such as allantoin or EDTA in combination with a particular retinoid, adapalene.

In patent WO 2006/037 552, the inventors add constituents to the formulation base such as interleukin-8 inhibitor to act on the irritation process.

In WO 2005/079 775, the inventors improve the tolerance of retinoids by adding idebenone or a derivative thereof.

Won et al, U.S. Pat. No. 5,955,109 incorporate a retinoid into porous microspheres (Microsponge®) to reduce the release of the retinoid into the layers of the skin, which gives rise to a decrease in the level of irritation by controlling the release kinetics of the active agent through the skin.

In patent WO 2005/039 532, the authors use a retinoid in an oil-in-water microemulsion for the purpose of improving the bioavailability. This microemulsion is composed of a phospholipid and of a sodium hyaluronate or modified hyaluronic acid.

Saurat et al. in patent FR 2 865 651 propose a combination of a retinoid with one or more hyaluronate fragments in a formulation for dermatological use in the case of treatments for which it is necessary to improve the condition of the skin.

Cattaneo in patent US 2005/0 281 886 discloses chitosan microparticles and nanoparticles containing a retinoid. These microparticles and nanoparticles generated by a high-viscosity chitosan reduce the irritant effect of the retinoids.

Many nanometric systems and many nanoencapsulation techniques exist in the prior art. The prior art especially discloses polymer nanocapsules using techniques of evaporation of organic solvent dissolving the polymer which thus forms a rigid wall of the nanocapsule. However, the presence of organic solvent may be a source of intolerance, or of toxicity problems.

The prior art, and especially patent CN 1 491 551, discloses nanocapsule formulations with ivermectin as active agent suspended in water and prepared via polymer emulsions, by means of a solvent-free process using in situ polymerization of monomer. The main drawback of encapsulation techniques via in situ polymerization and in particular interfacial polymerization is the generation of low molecular mass compounds as a result of risks of incomplete polymerization. Toxicity problems may thus be created due to the presence of these low masses.

Patents WO 01/64328 and WO 2011/036 234 disclose lipid nanocapsules containing phosphatidylcholines, but in combination with a hydrophilic co-surfactant derived from polyethylene glycol, which is necessary for producing the nanocapsules. The claimed process for preparing such nanocapsules proceeds via a phase inversion temperature (PIT process), which gives rise to the use of temperature cycles in the process. These techniques are therefore not applicable to the majority of retinoids, since they bring about degradation of the active agent. Moreover, in these same patents, nothing is suggested regarding the tolerance and stability of the active agent, such as a retinoid, in these compositions.

The problem that the present invention proposes to solve here is thus that of designing a physically and chemically stable composition containing at least one retinoid, for the treatment of dermatological pathologies, more particularly acne, said retinoid being in dissolved form, the composition according to the invention needing to improve the tolerance of the active principle while at the same time being easy to use and being cosmetically acceptable for application to any area of the body that might be affected by the pathology.

According to the invention, the term "physical stability" refers to a composition whose physical properties such as the organoleptic properties, pH and viscosity are stable over time and under various temperature conditions: 4° C., room temperature, 40° C.

According to the invention, the term "chemical stability" refers to a composition in which the active principle is chemically stable over time, irrespective of the temperature condition: 4° C., room temperature, 40° C.

According to the present invention, the retinoid must be in a dissolved form in a stable composition. Many retinoids often present solubilization difficulties. The retinoids according to the invention, and especially the retinoid preferentially used, have low solubility, thus limiting their incorporation into the vehicles cited in the preceding patents, and making it difficult to obtain a stable composition. Moreover, the addition of a solubilizer to topical formulations often increases the irritant power of the formulations.

In order to improve the tolerance of irritant retinoids and the stability of the active agent in an aqueous formulation for cutaneous application, the Applicant has discovered, surprisingly, that a composition which can modify the structure of the interface between the retinoid dissolution medium and the aqueous phase has an influence on the stability and the tolerance of the active principle in the composition. In the present invention, the retinoid is dissolved in the inner phase of lipid nanocapsules.

The term "lipid nanocapsules" means a nanovesicular system of nanometric size, i.e. less than a micrometre, consisting of a non-polymeric lipid envelope surrounding an oily core that is liquid or semiliquid at room temperature.

The term "room temperature" means a temperature between 15 and 25° C.

The term "oily core" or "lipid inner phase" means the inner phase of the lipid nanocapsules containing a water-immiscible lipophilic solvent.

The present invention thus relates to the formulation of lipid nanocapsules that can improve the cutaneous tolerance of retinoids, in the treatment of dermatological pathologies, especially acne.

The lipid nanocapsules may, moreover, allow targeting of the active agent by means of using objects of very small sizes.

Unlike liposomes, whose core is aqueous, the inner phase of the lipid nanocapsules of the present invention is lipophilic, allowing the dissolution of hydrophobic active principles in larger amount. The dissolution of hydrophobic active principles can only be made possible with liposomes via the membrane, generally consisting of phospholipids.

The present invention is a system for using lipid nanocapsules without the use of an organic solvent of alcoholic type often used for the formation of the envelope, thus limiting the risks of toxicity and intolerance and in particular of irritation.

According to the present invention, the composition comprises lipid nanocapsules rather than lipid nanospheres. In contrast, lipid nanospheres, also known as solid lipid nanoparticles (SLN), are matrix particles, i.e. all of their mass is solid at room temperature. When nanospheres contain a pharmaceutically acceptable active principle, it is finely dispersed or dissolved in the solid matrix. The lipid nanocapsules according to the invention are particles whose core is composed of one or more fatty substances that are liquid or semiliquid at room temperature, in which the active principle is dissolved, and whose envelope is of lipophilic and non-polymeric nature. Specifically, the lipid nanocapsules according to the invention do not require any polymer and therefore no in situ polymerization.

Moreover, the process for preparing the lipid nanocapsules according to the invention does not use any temperature cycle variations liable to degrade the active agent.

The Applicant has thus discovered, surprisingly, that compositions comprising at least one retinoid as irritant active principle in dissolved form in lipid nanocapsules in a hydrophilic environment, not requiring the use of polymer or of organic solvent, ensure the stability of the active agent and satisfactory tolerance of the composition. The composition according to the invention may also promote the cutaneous penetration of the active agent, which is useful in the treatment of dermatological complaints, especially acne.

A first subject of the present invention is thus lipid nanocapsules consisting of:
  at least one retinoid as irritant active principle;
  at least one oily inner phase in which the retinoid is dissolved;
  a non-polymeric envelope obtained from at least one surfactant; said nanocapsules not containing any organic solvent of alcoholic type.

A subject of the present invention is also a nanodispersion, composed of nanocapsules dispersed in a hydrophilic phase.

The term "nanodispersion" thus means the lipid system composed of lipid nanocapsules with a solid or semi solid interface, which are dispersed in a continuous hydrophilic phase, said nanocapsules containing an oily inner phase in which the irritant active principle, and especially the retinoid, is dissolved, an envelope obtained from a surfactant, forming the semi solid or solid interface between the oily inner layer and the continuous hydrophilic phase.

Said nanodispersion according to the invention is incorporated in a pharmaceutically acceptable vehicle, such as a gel, a solution or an emulsion, for instance a cream or a lotion.

The present invention thus also relates to a composition, especially a pharmaceutical composition, said composition comprising, in a pharmaceutically acceptable vehicle, the nanodispersion according to the invention.

The present invention thus relates to a pharmaceutical composition, said composition comprising, in a pharmaceutically acceptable vehicle, the nanodispersion composed of lipid nanocapsules dispersed in a hydrophilic phase, consisting of:
  at least one irritant active principle, preferably a retinoid;
  at least one oily inner phase in which the retinoid is dissolved without using any volatile organic solvent such as alcohols;
  a non-polymeric envelope obtained from at least one surfactant;
said nanocapsules not containing any organic solvent of alcoholic type.

According to the invention, the term "composition" thus means the nanodispersion, incorporated in a pharmaceutically acceptable vehicle, such as an excipient or a mixture of excipients that can form a composition in the form of a gel, a solution or an emulsion, for instance a cream or a sprayable or non-sprayable lotion.

In particular, the present invention thus relates to lipid nanocapsules prepared without organic solvent of alcoholic type.

According to the present invention, the term "lipid nanocapsules" means lipid nanosystems with a mean size of less than a micrometre, preferably less than 800 nm and preferably less than 500 nm.

The lipid nanocapsules are present in the composition according to the invention in an amount of between 0.1% and 30%, preferably between 0.5% and 20% and more particularly between 1% and 10% by weight relative to the total weight of the composition.

The nanocapsules each consist of a core that is liquid or semiliquid at room temperature containing the active principle, and of an envelope obtained from at least one surfactant.

The prior art (WO 01/64328 and WO 2011/036 234) discloses lipid nanocapsules containing phosphatidylcholines, but always in combination with a hydrophilic nonionic co-surfactant which is an oxyethylenated derivative of fatty alcohols and of fatty acids, namely the polyethylene glycol 2-hydroxystearate sold under the name Solutol® HS 15 by the company BASF.

In contrast with the prior art, the present invention relates to lipid nanocapsules containing phosphatidylcholines without lipophilic or hydrophilic co-surfactant.

The surfactant envelope encapsulating the core that is liquid or semiliquid at room temperature is preferably composed of a non-polymeric material that is rigid at room temperature and whose transition temperature or melting point is high. In order to be rigid at room temperature, the transition temperature or melting point must be greater than 35° C., preferably greater than 40° C. and ideally greater than 45° C.

In the nanocapsules according to the invention, the envelope consists of at least one lipophilic surfactant. Preferentially, the envelope consists of only one lipophilic surfactant; advantageously chosen from amphiphilic lipids. More preferentially, the surfactant is chosen from the family of lecithins or phosphatidylcholines or phospholipids. Phosphatidylcholines show good compatibility with the skin and have a very low irritant potential.

As lecithins that may be used, mention may be made especially of natural or synthetic or derived soybean or egg lecithins. The first type of lecithin is phosphatidylcholine (PC). Other types of lecithin exist, including phosphatidylglycerol, phosphatidylinositol, sphingomyelin and phosphatidylethanolamine.

Among the lecithins with a transition temperature of greater than 35° C., mention may be made of dipalmitoylphosphatidylcholine (DPPC), distearoylphosphatidylcholine (DSPC), dibehenylphosphatidylcholine (DBPC), palmitoylstearoylphosphatidylcholine (PSPC) palmitoylbehenylphosphatidylcholine (PSPC) and stearoylbehenylphosphatidylcholine (SBPC), and also any saturated lecithin with long chains of fatty acids and derivatives thereof.

The lecithins especially used in the present invention are solid at room temperature, which promotes the formation of a semisolid interface around the liquid or semiliquid core. This formulation allows the encapsulation of the active agent dissolved in the inner phase, more particularly the retinoid.

Preferably, among the family of lecithins with a high transition temperature, the lipophilic surfactant is a hydrogenated lecithin, advantageously with a high percentage of saturated (or hydrogenated) phosphatidylcholine. The term "high percentage" means an amount of greater than 85% of saturated (or hydrogenated) phosphatidylcholine relative to the total weight of lecithin.

The lipid nanocapsules according to the invention more particularly contain a semisolid or solid interface between the inner phase and the aqueous continuous phase, by means of using, as sole surfactant, a lecithin whose percentage of saturated phosphatidylcholine is high, said composition according to the invention being free of lipophilic or hydrophilic co-surfactant.

As lecithins preferentially used according to the invention, mention may be made of certain hydrogenated lecithins with a content of hydrogenated phosphatidylcholine of greater than 85%, for instance Lipoid® of grade S100-3 or SPC-3, Epikuron® of grade 200 SH or 100H, or Phospholipon® of grade 90H or 100H.

Preferentially, the lecithin used as sole surfactant is Phospholipon® 90H, for which the content of hydrogenated phosphatidylcholine is greater than 90% and comprising 85% distearoylphosphatidylcholine (DSPC) and 15% dipalmitatoylphosphatidylcholine (DPPC), and whose transition temperature is about 54° C.

The lipophilic surfactant surrounding the liquid or semiliquid core as defined above is present in an amount of between 0.01% and 10% by weight, preferably between 0.05% and 5% by weight and more preferentially between 0.1% and 1% by weight relative to the total weight of the composition.

The lipophilic surfactant, especially the hydrogenated lecithin, according to the invention enables by itself the encapsulation of the retinoid, which avoids contact of this active agent with the hydrophilic phase, and thus ensures its chemical stability. In particular, the composition, and especially the envelope, is free of lipophilic or hydrophilic co-surfactant.

The composition according to the invention thus comprises in the nanocapsules at least one active principle known to those skilled in the art as having an irritant nature. The irritant active principles that may preferentially be used according to the invention are retinoids. The retinoids that may be used in the context of the invention especially comprise all-trans-retinoic acid or tretinoin, 13-cis-retinoic acid or isotretinoin, acitretin, arotinoic acid, retinol, adapalene, tazarotene, retinaldehyde, etretinate and the compounds protected in patent application WO 2006/066 978 such as 3"-tert-butyl-4'-(2-hydroxyethoxy)-4"-pyrrolidin-1-yl-[1,1';3',1"]-terphenyl-4-carboxylic acid, the compounds of patent application FR 05/12367 including 2-hydroxy-4-[3-hydroxy-3-(5,6,7,8-tetrahydro-5,5,8,8-tetramethyl-2-naphthyl)-1-propynyl]benzoic acid or an enantiomer thereof, the compounds of patent application WO 05/56516 including 4'-(4-isopropylamino-butoxy)-3'-(5,5,8,8-tetramethyl-5,6,7,8-tetrahydronaphthalen-2-yl)-biphenyl-4-carboxylic acid, the compounds of patent application PCT/EP04/014809 including 4-{3-hydroxy-3-[4-(2-ethoxyethoxy)-5,5,8,8-tetramethyl-5,6,7,8-tetrahydronaphthalen-2-yl]-prop-1-ynyl}benzoic acid, and the compounds of patent application FR 2 861 069 including 4-[2-(3-tert-butyl-4-diethylaminophenyl)-2-hydroxyiminoethoxy]-2-hydroxybenzoic acid. 3"-tert-Butyl-4'-(2-hydroxyethoxy)-4"-pyrrolidin-1-yl-[1,1;3',1"]-terphenyl-4-carboxylic acid, as protected in patent application WO 2006/066 978, is particularly preferred. In the rest of the present patent application, 3"-tert-butyl-4'-(2-hydroxyethoxy)-4"-pyrrolidin-1-yl-[1,1';3',1"]-terphenyl-4-carboxylic acid, the preferred compound according to the invention, will also be referred to as compound A.

The composition according to the invention comprises between 0.00001% and 1% and preferably from 0.0001% to 0.5% by weight of at least one retinoid relative to the total weight of the composition, and preferentially the composition according to the invention contains from 0.001% to 0.05% by weight of a retinoid relative to the total weight of the composition. In a preferred embodiment according to the invention, the composition comprises between 0.001% and 0.05% and more particularly between 0.003% and 0.03% by weight of 3"-tert-butyl-4'-(2-hydroxyethoxy)-4"-pyrrolidin-1-yl-[1,1;3',1"]-terphenyl-4-carboxylic acid relative to the total weight of the composition.

The irritant active principle, especially the retinoid and more particularly 3"-tert-butyl-4'-(2-hydroxyethoxy)-4"-pyrrolidin-1-yl-[1,1;3',1"]-terphenyl-4-carboxylic acid, is thus in dissolved form in the core of the lipid nanocapsules according to the invention. Said core, or oily inner phase, comprises at least one fatty substance that is liquid or semi liquid at room temperature.

The composition of the inner phase is thus essential for the stability of the active principle. The oily inner phase must, of course, be compatible with the active agent to be dissolved, and be able to dissolve the active agent.

The term "phase that can dissolve the active agent" means a phase in which the active principle has a solubility strictly greater than 0.1%.

This oily inner phase thus comprises at least one oily solvent, chosen from triglycerides and oils containing the same, mineral oils, fatty acid esters, polyethoxylated fatty acids, fatty alcohols and corresponding esters, and glycols, with the exception of glycol ethers.

According to the invention, the oily inner phase does not contain any solvents of pure fatty acid type (i.e. in non-ethoxylated acid form).

The term "oily solvent" means any water-immiscible material of natural, animal or synthetic origin.

Among the triglycerides and oils containing the same, mention may be made in a nonlimiting manner of octanoic acid triglycerides or caprylic/capric acid triglycerides, such as those sold by the company Stéarineries Dubois or those sold under the names Miglyol® 810, 812 and 818 by the company Sasol.

Among the mineral oils, mention may be made in a nonlimiting manner of liquid paraffin.

Among the fatty acid esters, mention may be made in a nonlimiting manner of diisopropyl adipate and cetearyl isononanoate.

Among the fatty alcohols, mention may be made in a nonlimiting manner of octyldodecanol or octyldodecanol octanoate.

In a preferred embodiment according to the invention, the preferred oily inner phase that is a solvent for the active principle is diisopropyl adipate, such as the commercial product Crodamol® DA sold by the company Croda.

In addition to this or these oily solvent(s) the inner phase may also comprise one or more fatty substances that are liquid or semiliquid at room temperature and that cannot dissolve the active agent.

The term "fatty substance that cannot dissolve the active agent" means a compound in which the retinoid has a solubility of less than or equal to 0.1%.

Similarly, the oily inner phase may also contain one or more non-oily co-solvents, such as N-methyl-2-pyrrolidone or dimethyl isosorbide, or alternatively dimethyl sulfoxide, with the exception of glycol ethers.

According to a preferred embodiment according to the invention, the active principle is dissolved in the oily inner phase in the absence of any organic solvent, of alcoholic type such as ethanol, whereas the latter is generally necessary for the dissolution of an active principle such as retinoids (as described in US 2005/0 048 088).

In the oily inner phase, the preferred solvent, and more particularly diisopropyl adipate, will be present in an amount of between 50% and 99.997% by weight relative to the total weight of the inner phase; preferably in an amount of between 70% and 99.997% and preferably between 95% and 99.997% by weight relative to the total weight of the inner phase.

In the oily inner phase, the optional co-solvent or fatty substance is present in an amount of between 0% and 50% by weight relative to the total weight of the inner phase; preferably in an amount of between 0.1% and 25% and preferably between 0.5% and 10% by weight relative to the total weight of the inner phase.

In the nanodispersion according to the invention, the oily inner phase of the nanocapsules is present in an amount of between 0.1% and 50% by weight relative to the total weight of the nanodispersion, preferably in an amount of between 0.5% and 30% and preferably between 1% and 10% by weight relative to the total weight of the nanodispersion.

In the nanodispersion according to the invention, the ratio between the oily inner phase and the amount of lecithin is between 5/1 and 10/1. Preferably, this ratio is between 6/1 and at 8/1 and preferentially equal to 7/1.

In the nanodispersion, the nanocapsules are dispersed in a hydrophilic phase. The continuous hydrophilic phase comprises water. This water used may be demineralized water, a floral water such as cornflower water, or a natural spring water or mineral water, chosen, for example, from Vittel water, Vichy basin water, Uriage water, Roche Posay water, Bourboule water, Enghien-les-Bains water, Saint Gervais-les-Bains water, Néris-les-Bains water, Allevard-les-Bains water, Digne water, Maizièeres water, Neyrac-les-Bains water, Lons-le-Saunier water, Eaux Bonnes water, Rochefort water, Saint Christau water, Fumades water, Tercis-les-Bains water, Avèene water or Aix-les-Bains water.

The water may be present in a content of between 55% and 95% by weight and preferably between 60% and 95% by weight relative to the total weight of the composition.

One subject of the present invention is thus a composition, especially a pharmaceutical composition, said composition comprising the nanodispersion containing the lipid nanocapsules defined above in the context of the present invention in a pharmaceutically acceptable vehicle, such as a gel, a solution or an emulsion, for instance a cream or a lotion.

When the pharmaceutically acceptable vehicle is a gel, the nanodispersion is dispersed in a hydrophilic phase which comprises at least one gelling agent. This gelling agent is preferably a cellulose derivative chosen from semi-synthetic cellulose-based gelling agents, such as methylcellulose, ethylcellulose, hydroxypropylmethylcellulose, hydroxyethylcellulose, carboxymethylcellulose, hydroxymethylcellulose or hydroxypropylcellulose, taken alone or as a mixture. Hydroxypropylmethylcellulose or hydroxyethylcellulose is preferably used. These compounds are especially sold by the company Colorcon under the name Methocel® (for example: Methocel® E4M) or by the company Ashland under the name Natrosol® (for example: Natrosol® 250 HHX). The gelling agent may also be chosen from natural gums such as gum tragacanth, guar gum, acacia gum, gum arabic, xanthan gum, starch and derivatives thereof, biopolymers such as sodium alginate, pectin, dextrin, chitosan or sodium hyaluronate, and derivatives thereof, taken alone or as a mixture. The gelling agent may also be chosen from copolymers of polyacrylic acid and of methyl methacrylate sold, for example, under the name Carbopol® or Pemulen® by the company Lubrizol, and also copolymers thereof such as Ultrez® 10 or 20, carboxyvinyl polymers, polyvinylpyrrolidones and derivatives thereof, and polyvinyl alcohols. The gelling agent may also be chosen from the compound Sepigel 305 consisting of a polyacrylamide/C13-C14 isoparaffin/laureth-7 mixture, or Simulgel® 600PHA or Sepineo® P600, namely sodium acryloyldimethyltaurate copolymer/isohexadecane/polysorbate 80, these two products being sold by the company SEPPIC.

The gelling agent is especially used in a concentration of between 0.1% and 10% by weight and preferably between 0.1% and 5% by weight relative to the total weight of the composition.

When the pharmaceutically acceptable vehicle is a solution, the nanodispersion is dispersed in a vehicle composed of a hydrophilic or aqueous phase.

The term "hydrophilic phase which constitutes the pharmaceutically acceptable vehicle" means any hydrophilic phase as defined previously in the present invention.

When the pharmaceutically acceptable vehicle is a cream or a lotion, the nanodispersion is dispersed in a vehicle composed of a hydrophilic phase and of a fatty phase optionally comprising at least one surfactant or emulsifier.

In this case, of pharmaceutical vehicles in cream or lotion form, the composition according to the invention thus comprises a fatty phase. This fatty phase may comprise, for example, plant oils, mineral oils, animal oils, synthetic oils or silicone oils, and mixtures thereof.

The fatty phase of the invention comprises:
  one or more mineral oils, for instance liquid paraffins of different viscosities, for instance Marcol® 152, Marcol® 52 or Primol® 352 sold by Univar, one or more plant oils, among which mention may be made of sweet almond oil, palm oil, soybean oil, sesame oil, sunflower oil, hydrogenated castor oil or coconut oil, one or more synthetic oils, among which mention may be made of apricot kernel oil PEG-6 ester (Labrafil® M1944CS), propylene glycol laurate (Lauroglycol® FCC), propylene glycol monocaprylate (Capryol® 90) sold by Gattefossé, triglycerides, for instance capric/caprylic acid triglycerides under the name Miglyol® 812 is sold by the company Sasol, esters such as C12-C15 alkyl benzoate (Crodamol® AB sold by Croda) or cetearyl isononanoate, for instance the product sold under the name Kollicream® CI by the company BASF France, and also PPG-15 stearyl ether such as Arlamol® PS15E, or isopropyl palmitate, for instance the product sold under the name Crodamol® IPP by the company Croda, one or more animal oils, among which mention may be made of lanolin, squalene, fish oil, mink oil, with, as a derivative, the squalane sold under the name Cosbiol® by the company Laserson, one or more silicone oils for improving the properties of the formula on application, such as cyclomethicone (St-Cyclomethicone 5NF®) or dimethicone (Q7 9120® Silicon Fluid having a viscosity from 20 cSt to 12 500 cSt from Dow Corning), one or more fatty-phase thickeners of fatty alcohol type, such as cetyl alcohol (Crodacol C70 supplied by Croda/Lanette 16 sold by BASF, but also Kolliwax® CA sold by BASF), cetearyl alcohol (Crodacol 1618 sold by Croda, Tego Alkanol® 1618 sold by Evonik, but also Kolliwax® CSA 50 sold by BASF), stearyl alcohol (Crodacol® S95 sold by Croda, Kolliwax® SA sold by Cognis, but also Tego Alkanol® 18 sold by Evonik), but also behenyl alcohol (Lanette® 22 sold by BASF, Nacol® 22-98 sold by Sasol, but also Behenyl Alcohol® 65 80 sold by Nikko Chems), or of carnauba wax type sold by Baerlocher, but also the beeswax sold under the name Cerabeil Blanchie DAB® sold by Univar, and glyceryl tribehenate such as Compritol® 888 sold by Gattefossé. In this case, a person skilled in the art will adjust the heating temperature of the preparation according to the presence or absence of these solids.

Thus, the fatty phase of the cream or lotion according to the invention may be present in a content of between 1% and 95% by weight, preferably between 5% and 85% and more preferentially between 15% and 50% by weight relative to the total weight of the composition.

Preferably, when the vehicle of the composition according to the invention is a cream or lotion, the emulsion is in the form of an oil-in-water (O/W) emulsion. This emulsion may or may not comprise at least one emulsifier.

In the case of a cream or a lotion comprising at least one emulsifier, the preferred concentrations are between 0.001% and 20% by weight relative to the total weight of the composition. More preferably, the concentration is between 1% and 15% and preferably between 3% and 11% by weight relative to the total weight of the composition.

The emulsifying power of emulsifiers is closely linked to the polarity of the molecule. This polarity is defined by the HLB (hydrophilic/lipophilic balance).

A high HLB indicates that the hydrophilic fraction is predominant and, conversely, a low HLB indicates that the lipophilic portion is predominant. For example, HLB values of greater than about 10 correspond to hydrophilic emulsifiers.

Emulsifiers may be classified, according to their structure, under the generic terms "ionic" (anionic, cationic or amphoteric) or "nonionic". Nonionic emulsifiers are emulsifiers that do not dissociate into ions in water and are therefore insensitive to variations in pH.

Nonionic emulsifiers are particularly suited for preparing the emulsions of oil-in-water type that are the subject of the present invention. Thus, the emulsifying system, which is a component of the emulsion of the invention, comprises at least one nonionic emulsifier, with a predominant hydrophilic fraction, i.e. having a high HLB, of greater than about 10.

Mention may be made, as nonlimiting examples of nonionic emulsifiers exhibiting a high HLB, of sorbitan esters, such as POE(20) sorbitan monooleate, sold under the name of Tween®80 (HLB=15), or POE(20) sorbitan monostearate, sold under the name of Tween 60® (HLB=14.9), fatty alcohol ethers, such as POE(21) stearyl ether (HLB=15.5), sold under the name Brij 721® by the company Croda, or ceteareth-20, sold under the name Eumulgin®B2 (HLB of 15.5) by the company BASF, polyoxyethylene glycol esters, such as glyceryl stearate and PEG 100 stearate, sold under the name Arlacel®165 FL (HLB=11) by the company Croda, or PEG 6 stearate and PEG 32 stearate, sold under the name Tefose®1500 (HLB=10) by the company Gattefossé, or sugar esters with a high HLB, such as PEG 20 methyl glucose sesquistearate, sold under the name Glucamate® SSE20 (HLB=15) by the company Amerchol, and sucrose laurate, sold under the name Surfhope C-1216é (HLB=16), and sucrose stearate, sold under the name Surfhope C-1811® (HLB=11) by the company Gattefossé. Preferably, said nonionic emulsifiers of high HLB have an HLB of between 10 and 18.

Mention will be made, as nonlimiting examples of nonionic emulsifiers exhibiting a low HLB (lipophilic emulsifiers), of sorbitan esters, such as sorbitan monostearate (HLB=4.7), sold under the name Span® 60 by the company Croda, glycerol esters, such as glycerol monostearate, sold under the name Kolliwax® GMS II (HLB=3.8) by the company BASF, polyethylene glycol esters, such as PEG-6 isostearate, sold under the name Olepal isostéarique® (HLB=8) by the company Gattefossé, or sugar esters with a low HLB, such as methyl glucose sesquistearate, sold under the name Glucate SS® (HLB=6) by the company Amerchol, and sucrose dilaurate, sold under the name Surfhope® C 1205 (HLB=5), and sucrose tristearate, sold under the name Surfhope® C-1803 (HLB=3), by the company Gattefossé.

Preferably, said nonionic emulsifiers of low HLB have an HLB of less than 10.

The nonionic emulsifiers may be used alone or as a mixture of two or more of them to form the emulsifying system that is a component of the cream or lotion of the invention.

Preferably, use will be made, as emulsifying system, of one or more "nonionic emulsifier of high HLB"/"nonionic emulsifier of low HLB" couples; this may in particular be a nonionic emulsifying system comprising at least one nonionic emulsifier with an HLB of greater than about 10 and at least one nonionic surfactant with an HLB of less than about 10.

The ratio of each of the two emulsifiers forming the abovementioned couple is most commonly determined by calculating the required HLB of the fatty phase used.

Preferred emulsifiers that may be mentioned include hydrophilic emulsifiers of the type such as glyceryl stearate & PEG-100 stearate sold under the name Arlacel® 165FL by the company Croda; PEG-6 stearate and PEG-32 stearate sold under the name Tefose® 1500 by Gattefossé, PEG-20 methyl glucose sesquistearate sold under the name Glucamate® SSE 20 by Amerchol, polyoxyethylene (21) stearyl ether sold under the name Brij® 721 by Croda, and Ceteareth 20 sold under the name Kolliphor® CS20 by BASF; lipophilic emulsifiers of the type such as methyl glucose sesquistearate, such as Glucate® SS sold by Lubrizol.

Emulsifiers are amphiphilic compounds which contain a hydrophobic portion with affinity for oil and a hydrophilic portion with affinity for water, thus creating a link between the two phases. The ionic or nonionic emulsifiers thus stabilize the O/W emulsions by becoming adsorbed at the water/oil interface and by forming a film or lamellar layers.

The cream or lotion according to the invention also comprises a hydrophilic phase or aqueous phase.

The term "hydrophilic phase which constitutes the pharmaceutically acceptable vehicle, alone or in an emulsion" means any hydrophilic phase as defined previously in the present invention.

The composition according to the invention may also contain, in the nanodispersion or the pharmaceutically acceptable vehicle, additives or combinations of additives, such as:

preserving agents;
pro-penetrants;
stabilizers;
humectants;
humidity regulators;
pH regulators;
osmotic pressure modifiers;
chelating agents;
UV-A and UV-B screening agents;
and antioxidants.

Among the pro-penetrating agents that may be used according to the invention, mention may be made especially of glycols, for instance propylene glycol, glycol ethers, N-methyl-2-pyrrolidone, or dimethyl sulfoxide, with the exception of glycol ethers.

Among the preserving agents that may be used according to the invention, mention may be made especially of methyl paraben, propyl paraben, benzalkonium chloride, phenoxyethanol sold under the name Phenoxetol® by Clariant, benzyl alcohol sold under the name benzyl alcohol by Merck, sodium benzoate sold under the name Probenz® SP by Unipex, potassium sorbate sold under the name potassium sorbate by VWR, benzoic acid sold under the name benzoic acid by VWR, 2-bromo-2-nitropropane-1,3-diol sold under the name Bronopol® by Jan Dekker International, chlorhexidine sold under the name Chlorexidine digluconate 20% solution by Arnaud Pharmacie, chlorocresol and derivatives thereof, ethyl alcohol and diazolidinylurea. These preservatives can be used alone or in combination in order to efficiently protect the formulae against any bacterial contamination.

The preserving agents preferentially used in the invention are methyl paraben, propyl paraben, benzyl alcohol, phenoxyethanol and potassium sorbate. They can be used at from 0.01% to 5% and preferentially from 0.05% to 2%.

Needless to say, a person skilled in the art will take care to select the optional compound(s) to be added to these compositions such that the advantageous properties intrinsically associated with the present invention are not, or are not substantially, adversely affected by the envisaged addition.

These additives may be present in the composition from 0 to 95% by weight relative to the total weight of the composition.

The composition according to the invention thus comprises, in a pharmaceutically acceptable vehicle, on a weight basis relative to the total weight of the composition, nanocapsules composed of:
  a) 0.01% to 10% of surfactant chosen from amphiphilic lipids;
  b) 0.1% to 50% of fatty substance that is liquid or semiliquid at room temperature;
  c) 0.00001% to 0.3% of at least one retinoid.

The composition according to the invention thus preferably comprises, in a pharmaceutically acceptable vehicle, on a weight basis relative to the total weight of the composition, nanocapsules composed of:
  a) 0.1% to 5% of surfactant chosen from amphiphilic lipids, preferably lecithin;
  b) 1% to 20% of fatty substance that is liquid or semiliquid at room temperature, preferably fatty acid esters;
  c) between 0.00001% and 0.1% of at least one retinoid, preferably 3"-tert-butyl-4'-(2-hydroxyethoxy)-4"-pyrrolidin-1-yl-[1,1';3',1"]-terphenyl-4-carboxylic acid.

In a preferred embodiment according to the invention, the composition comprises, in a pharmaceutically acceptable vehicle, on a weight basis relative to the total weight of the composition:
  a) 0.1% to 5% of lecithin;
  b) 1% to 5% of fatty acid esters;
  c) 0.001% to 0.03% of 3"-tert-butyl-4'-(2-hydroxyethoxy)-4"-pyrrolidin-1-yl-[1,1;3',1"]-terphenyl-4-carboxylic acid.

The pharmaceutical composition that may be used according to the invention is intended for treating the skin and may be administered topically, parenterally or orally.

Via the oral route, the pharmaceutical composition may be in liquid or pasty form, and more particularly in the form of gel capsules, coated tablets or syrups.

Via the parenteral route, the composition may be in the form of suspensions for perfusion or for injection.

Preferably, the composition is administered topically. The term "topical application" means application to the skin, mucous membranes, the hair or the scalp.

Via the topical route, the composition may be in liquid or pasty form, and more particularly in the form of creams, milks, pomades, impregnated pads, syndets, wipes, gels, sprays, foams, lotions, sticks, shampoos or washing bases.

A subject of the invention is also a composition for improving the tolerance of an irritant active principle, comprising at least one irritant active principle, characterized in that it comprises, in a pharmaceutically acceptable vehicle, lipid nanocapsules dispersed in a hydrophilic phase, said lipid nanocapsules containing an oily inner phase in which the irritant active principle is dissolved, and a non-polymeric envelope obtained from at least one surfactant chosen from amphiphilic lipids, said composition not containing any fatty acids.

In a preferred embodiment according to the invention, the invention also relates to a composition for improving the tolerance of a dissolved irritant active principle, characterized in that the irritant active principle is dissolved in the absence of a co-solvent of alcoholic type such as ethanol.

A subject of the invention is also a process for preparing compositions comprising at least one retinoid, preferably 3"-tert-butyl-4'-(2-hydroxyethoxy)-4"-pyrrolidin-1-yl-[1,1; 3',1"]terphenyl-4-carboxylic acid or compound A. This process makes use of a high-pressure homogenizer (HPH). In particular, the process according to the invention does not use a phase inversion temperature (PIT) (used especially in patents FR 2 805 761 and FR 2 840 531), and therefore does not require temperature increase and decrease cycles. Specifically, the process according to the invention is performed in the HPH without heating; the HPH therefore does not require successive heating and cooling, and is not temperature-regulated.

The process may be defined in the following various manufacturing steps:

1—Preparation of the Nanodispersion.

a) Dissolution of the Active Principle:

The active principle is dissolved in the oily core or inner oily phase comprising, inter alia, the oil for dissolving the active principle, in a suitable container and using a magnetic bar.

The hydrogenated phosphatidylcholine used is dispersed in this same oily phase heated to about 75° C.

b) Preparation of the Aqueous Phase

All of the aqueous phase is heated to 75° C. in a suitable container.

A preserving agent or other additive may be added to this phase.

c) Mixing of the Phases and Prehomogenization

Once the two phases are at the nominal temperature, they are mixed together with stirring (homogenization with an Ultra-Turrax® blender for a minimum of 2 minutes at 8000 rpm). Once this prehomogenization has been performed, the nanodispersion is introduced into the HPH (high-pressure homogenizer).

d) High-Pressure Homogenization

The use of a high-pressure homogenizer makes it necessary to set the number of passes through the homogenization chamber and the homogenization pressure.

The homogenization process is then applied:
  500 bar minimum up to 1000 bar of homogenization pressure in the homogenization chamber,
  between 5 and 10 passes through the homogenization chamber.

During the passes through the homogenization chamber, the nanodispersion is not heated, and the HPH system is not temperature-controlled.

2—Incorporation of the Nanodispersion into the Pharmaceutically Acceptable Vehicle.

In the case of a gel, the nanodispersion gelation step takes place at the end of manufacture after the various passes through the HPH, during the cooling of the nanodispersion.

A gel base is formulated to dilute the nanodispersion, and thus to obtain a gelled nanodispersion so as to facilitate application to the skin.

In the case of a solution, the nanodispersion may or may not be diluted in a hydrophilic phase.

In the case of a cream or a lotion, the cream or lotion is prepared beforehand. Nanodispersion is then incorporated into the finished vehicle.

The process may be adapted by a person skilled in the art according to the various ingredients used so as to maintain the stability of the nanodispersion in the final composition.

The composition according to the invention may be used as a medicament.

In particular, a subject of the invention is also a composition for its use in the treatment of dermatological complaints, especially human complaints, as defined below.

1) dermatological conditions associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;

2) keratinization disorders, in particular ichthyosis, ichthyosiform conditions, lamellar ichthyosis, Darier's disease, palmoplantar keratoderma, leukoplakia, pityriasis rubra pilaris and leukoplakiform conditions, cutaneous or mucosal (buccal) lichen;

3) dermatological conditions with an inflammatory immunoallergic component, with or without a cell proliferation disorder, and in particular all forms of psoriasis, whether cutaneous, mucosal or ungual, and even psoriatic arthritis, or else atopic dermatitis and the various forms of eczema;

4) skin disorders caused by exposure to UV radiation, and also for repairing or combating skin aging, whether it is photo-induced or chronological, or for reducing actinic keratoses and pigmentations, or any pathological condition associated with chronological or actinic aging, such as xerosis, pigmentations and wrinkles;

5) any condition associated with benign dermal or epidermal proliferations, whether or not they are of viral origin, such as common warts, flat warts, molluscum contagiosum and epidermodysplasia verruciformis, or oral or florid papillomatoses;

6) dermatological disorders such as immune dermatoses, for instance lupus erythematosus, bullous immune diseases and collagen diseases, such as scleroderma;

7) stigmata of epidermal and/or dermal atrophy induced by local or systemic corticosteroids, or any other form of cutaneous atrophy;

8) healing disorders, or for preventing or repairing stretch marks, or else for promoting healing;

9) in the treatment of any condition of fungal origin at the cutaneous level, such as *tinea pedis* and *tinea versicolor*;

10) pigmentation disorders, such as hyperpigmentation, melasma, hypopigmentation or vitiligo;

11) cutaneous or mucosal cancerous or precancerous conditions, such as actinic keratoses, Bowen's disease, in-situ carcinomas, keratoacanthomas and skin cancers such as basal cell carcinoma (BCC), squamous cell carcinoma (SCC) and cutaneous lymphomas such as T lymphoma.

Preferentially, the composition according to the invention is a composition for use in the treatment of acne, ichthyosis, ichthyosiform conditions, palmoplantar hyperkeratosis or psoriasis.

In a particularly preferred manner, the composition according to the invention will comprise Compound A for treating acne, ichthyosis, ichthyosiform conditions, palmoplantar hyperkeratosis or psoriasis.

Various composition formulations comprising a retinoid will now be given, as illustrations and with no limiting nature.

EXAMPLE 1

Solubility Data for Compound a in Various Oily Phases

The object of this preformulation study is to identify oily phases in which compound A has a solubility of greater than 0.1% m/m and in which it is chemically stable.

The stability of the active agent was evaluated by liquid chromatography coupled to a UV detector (HPLC-UV).

| INCI name (trade name) | Maximum solubility (% m/m) | Stability |
|---|---|---|
| Propylene glycol monocaprylate (Capryol ® 90) | 0.802 | 6 months RT/40° C. |
| Propylene glycol monolaurate (Lauroglycol ® FCC) | 0.296 | 6 months RT/40° C. |
| Diisopropyl adipate (Crodamol ® DA) | 0.297 | 6 months RT/40° C. |
| Macrogol oleate (Labrafil ® M1944CS) | 0.156 | 6 months RT/40° C. |
| Octyldodecanol (Eutanol ® G) | 0.137 | Unstable |
| Propylene glycol dicaprylate/dicaprate (Myritol ® PC) | 0.069 | Unstable |
| Caprylic/capric acid triglycerides (Miglyol ®812N) | 0.019 | 6 months RT/40° C. |

-continued

| INCI name (trade name) | Maximum solubility (% m/m) | Stability |
|---|---|---|
| Sweet almond oil | 0.011 | 6 months RT/40° C. |
| Mineral oil | 0.0001 | |

* RT: Room temperature

Following the results of this solubility and stability study, diisopropyl adipate appears to be a suitable solvent for obtaining the desired concentrations of compound A in the pharmaceutically acceptable vehicle.

EXAMPLE 2

Composition of the Nanodispersion Containing the Lipid Nanocapsules before Dilution in the Chosen Pharmaceutical Vehicle Containing Compound A

| Ingredients INCI name | Ingredients Trade name | Content (% m/m) |
|---|---|---|
| Hydrogenated phosphatidylcholine | Phospholipon 90H | 2.00 |
| Diisopropyl adipate | Crodamol DA | 13.77 |
| Methyl paraben | Nipagin M | 0.20 |
| Purified water | — | 84.0 |
| Compound A | — | 0.0276 |

EXAMPLE 3

Examples of Compositions of Gel Type According to the Invention Containing Compound A In order to prepare compositions of gel type according to the invention, various amounts of the nanodispersion prepared according to Example 2 were taken and diluted in a gel base consisting of water plus gelling agent.

To obtain a gel containing 0.01% active principle, 36.23% of the solution of lipid nanocapsules according to Example 2 was diluted in the gel base.

To obtain a gel containing 0.003% active principle, 9.2% of the solution of lipid nanocapsules according to Example 2 was diluted in the gel base.

Examples of compositions of gel type obtained according to the invention are thus as follows, qualitatively and quantitatively:

| Ingredients INCI name | Ingredients Trade name | Compositions (% m/m) | | | | |
|---|---|---|---|---|---|---|
| | | No. | No. 2 | No. 3 | No. 4 | No. 5 |
| Compound A | — | 0.01 | 0.003 | 0.01 | 0.003 | 0.01 |
| Diisopropyl adipate | Crodamol DA | 4.96 | 1.27 | 4.96 | 1.27 | 4.96 |
| Hydrogenated phosphatidylcholine | Phospholipon 90H | 0.72 | 0.18 | 0.72 | 0.18 | — |
| | Lipoid S100-3 | — | — | — | — | 0.80 |
| Methyl paraben | Nipagin N | 0.20 | 0.20 | 0.20 | 0.20 | 0.20 |
| Hydroxyethylcellulose | Natrosol 250 HHX | 0.80 | 0.80 | — | — | — |
| Polyacrylamide (and) C13-14 Isoparaffin (and) Laureth-7 | Sepigel 305 | — | — | 1.0 | 1.0 | — |
| Acrylamide, AMPS Copolymer Dispersion 40%/Isohexadecane | Simulgel 600PHA | — | — | — | — | 1.0 |
| Purified water | — | qs 100 | qs 100 | qs 100 | qs 100 | qs 100 |

*qs: quantity sufficient for

EXAMPLE 4

Physical Stability Studies on the Nanodispersion According to Example 2

The lipid nanocapsules of Example 2 were placed under various stability conditions: 4° C., room temperature and 40° C. The size of these lipid nanocapsules was monitored during the stability study by particle size analysis using a Nano-ZS Nanoseries Zetasizer (Malvern).

Two dilutions are used to perform the particle size analyses:
  1d: 10 µl of the nanodispersion in 15 ml of filtered distilled water
  2d: 1 mL of 1d in 5 mL of distilled water The solution of lipid nanocapsules has two particle size populations, the numerical majority fraction of which is of the order of a hundred nanometers.

| T0 particle size | Size (nm) | 132 | 650 |
|---|---|---|---|
| | CV % | 6.5 | 45 |
| | Numerical % | >99% | <1% |

| Temperature stability | | 4° C. | | Room temperature | | 40° C. | |
|---|---|---|---|---|---|---|---|
| T 2 months | Size (nm) | 117 | 434 | ND* | | 154 | 794 |
| | CV % | 8 | 30 | ND | | 15 | 40 |
| T 3 months | Size (nm) | 126 | 617 | 136 | 526 | 138 | 540 |
| | CV % | 10 | 25 | 9 | 30 | 9 | 30 |

ND: not done

After 3 months of maintenance of the nanodispersion under the stability conditions, irrespective of the temperature, the particle size of the lipid nanocapsules remains stable relative to the initial time.

EXAMPLE 5

Chemical Stability Studies on the Active Agent in Compositions 1 and 2 According to Example 3

Compositions 1 and 2 according to Example 3 were placed under various stability conditions: 4° C., room temperature and 40° C., and were monitored for 6 to 7 months. At each stability checkpoint, compound A was assayed by HPLC-UV.

Composition 1 (0.01% Retinoid, i.e. 0.1 mg/g)

| T0 | mg/g | 0.091 |
| | % RDS | 1.3 |
| | % expected titer | 91 |

| Temperature stability | | 4° C. | Room temperature | 40° C. |
|---|---|---|---|---|
| T 1 month | mg/g | 0.091 | ND | 0.097 |
| | % RDS | 0.2 | — | 0.8 |
| | % overlap | 100.0 | — | 106.6 |
| T 2 months | mg/g | ND | ND | 0.091 |
| | % RDS | — | — | 2.0 |
| | % overlap | — | — | 100 |
| T 3 months | mg/g | 0.098 | ND | 0.097 |
| | % RDS | 0.4 | — | 0.1 |
| | % overlap | 107.7 | — | 106.6 |
| T 3.5 months | mg/g | ND | 0.094 | 0.091 |
| | % RDS | — | 0.4 | 1.6 |
| | % overlap | — | 104 | 100 |
| T 7 months | mg/g | 0.096 | 0.093 | ND |
| | % RDS | 1.6 | 3.5 | — |
| | % overlap | 105.5 | 102.2 | — |

ND: not done

Composition 2 (0.003% Retinoid, i.e. 0.03 mg/g)

| T0 | mg/g | 0.028 |
| | % RDS | 0.5 |
| | % expected titer | 94 |

| Temperature stability | | 4° C. | Room temperature | 40° C. |
|---|---|---|---|---|
| T 1 month | mg/g | 0.028 | ND | 0.028 |
| | % RDS | 0.1 | — | 0.5 |
| | % overlap | 100.0 | — | 100.0 |
| T 3 months | mg/g | 0.028 | ND | 0.027 |
| | % RDS | 2.5 | — | 1.0 |
| | % overlap | 100.0 | — | 96.4 |
| T 4 months | mg/g | 0.028 | ND | 0.027 |
| | % RDS | 2.5 | — | 1.0 |
| | % overlap | 100 | — | 96 |
| T 4 months | mg/g | ND | 0.029 | 0.028 |
| | % RDS | — | 0.4 | 0.3 |
| | % overlap | — | 103.6 | 100.0 |
| T 6 months | mg/g | 0.029 | ND | 0.027 |
| | % RDS | 0.0 | — | 1.9 |
| | % overlap | 103.6 | — | 96.4 |

ND: not done

Conclusion: Compound A is chemically stable under the three temperature conditions: 4° C., room temperature and 40° C., in the gel compositions according to the invention for up to 6 to 7 months.

EXAMPLE 6

HPH Process for Manufacturing Compositions 1 and 2 of Example 3

To prepare 300 g of formulation with the high-pressure homogenizer (HPH):

Preparation of a solution containing 0.2% of compound A in Crodamol DA.

Heat all of the solution prepared previously: 41.40 g to about 70-75° C.

Incorporate portionwise with stirring (small deflocculator) all of the Phospholipon 90H: 6 g.

Keep stirring until a homogeneous mixture is obtained.

In parallel, heat the amount of formulation water: 252 g, with gentle stirring, and dissolve therein the methyl paraben: 0.6 g.

Once the two phases are homogeneous and at the same temperature (70° C.), incorporate the oily phase containing the active principle and Phospholipon 90H in water with stirring using an Ultra-Turrax blender at 8000 rpm.

Maintain this stirring for 2 minutes.

Pour this mixture into the HPH.

Switch on the manometer and start circulating the mixture in the HPH, taking care to separate out the water remaining in the machine circuit before recovering the formulation for recirculation.

Once the HPH circuit contains the mixture, set the desired pressure value on the manometer: between 700 and 900 bar.

The number of passes is set at 10 with recirculation of the mixture obtained at the HPH outlet.

Once the solution of lipid capsules has been obtained, 36.24% of this solution is added to 63.76% of Natrosol gel to obtain the desired viscosity and dilution for formulation 1 of Example 3 containing 0.01% active agent.

Once the solution of lipid capsules has been obtained, 10.87% of this solution is added to 63.76% of Natrosol gel to obtain the desired viscosity and dilution for formulation 2 of Example 2 containing 0.003% active agent.

EXAMPLE 7

Other Formulations of Gel Type According to the Invention Containing Tretinoin

| | Compositions (% m/m) | | | | |
|---|---|---|---|---|---|
| Ingredients | No. 6 | No. 7 | No. 8 | No. 9 | No. 10 |
| Tretinoin | 0.01 | 0.05 | 0.01 | 0.05 | 0.01 |
| Caprylic/capric acid triglycerides | 5.0 | 1.5 | 5.0 | 1.5 | 5.0 |
| Butyl hydroxytoluene | 0.10 | 0.10 | 0.10 | 0.10 | 0.10 |
| Hydrogenated phosphatidylcholine (Phospholipon 90H) | 0.72 | 0.22 | 0.72 | 0.22 | — |
| Hydrogenated phosphatidylcholine (Lipoid S100-3) | — | — | — | — | 0.72 |
| Methyl paraben | 0.20 | 0.20 | 0.20 | 0.20 | 0.20 |
| Hydroxyethylcellulose (Natrosol 250HHX) | 0.80 | 0.80 | — | — | — |
| Polyacrylamide (and) C13-14 Isoparaffin (and) Laureth-7 (Sepigel 305) | — | — | 0.80 | 0.80 | — |

-continued

| Ingredients | Compositions (% m/m) | | | | |
|---|---|---|---|---|---|
| | No. 6 | No. 7 | No. 8 | No. 9 | No. 10 |
| Acrylamide, AMPS Copolymer Dispersion 40%/Isohexadecane (Simulgel 600PHA) | — | — | — | — | 0.70 |
| Purified water | qs 100 | qs 100 | qs 100 | qs 100 | qs 100 |

EXAMPLE 8

Examples of Compositions of Emulsifier-free Cream Type According to the Invention Containing Compound A In order to prepare compositions of emulsion type according to the invention not containing any emulsifier, various amounts of the nanodispersion prepared according to Example 2 were taken and diluted in the cream prepared beforehand.

To obtain a cream containing 0.01% active principle, 36.23% of the solution of nanocapsules to according to Example 2 was diluted in the cream base.

To obtain a cream containing 0.003% active principle, 9.2% of the solution of nanocapsules according to Example 2 was diluted in the cream base.

| Ingredients | Compositions (% m/m) | | | | |
|---|---|---|---|---|---|
| | No. 11 | No. 12 | No. 13 | No. 14 | No. 15 |
| Compound A | 0.01 | 0.003 | 0.01 | 0.003 | 0.01 |
| Diisopropyl adipate (Crodamol DA) | 4.96 | 1.27 | 4.96 | 1.27 | 4.96 |
| Hydrogenated phosphatidylcholine (Phospholipon 90H) | 0.72 | 0.18 | 0.72 | 0.18 | — |
| Hydrogenated phosphatidylcholine (Lipoid S100-3) | — | — | — | — | 0.80 |
| Glycerol | 5.0 | 5.0 | 5.0 | 5.0 | 5.0 |
| Decamethylcyclopentasiloxane (ST-Cyclomethicone 5NF) | 7.0 | 7.0 | 7.0 | 7.0 | 7.0 |
| Propylene glycol | 6.0 | 6.0 | 6.0 | 6.0 | 6.0 |
| Methyl paraben (Nipagin M) | 0.2 | 0.2 | 0.2 | 0.2 | 0.2 |
| Phenoxyethanol | 1.0 | 1.0 | 1.0 | 1.0 | 1.0 |
| Polyacrylamide (and) C13-14 Isoparaffin (and) Laureth-7 (Sepigel 305) | — | — | 4.0 | 4.0 | — |
| Acrylamide, AMPS Copolymer Dispersion 40%/Isohexadecane (Simulgel 600PHA) | 4.0 | 4.0 | — | — | 4.0 |
| Purified water | qs 100 | qs 100 | qs 100 | qs 100 | qs 100 |

EXAMPLE 9

Examples of Compositions of Cream Type Containing at Least One Emulsifier According to the Invention Containing Compound A In order to prepare compositions of cream type containing at least one emulsifier according to the invention, various amounts of the nanodispersion prepared according to Example 2 were taken and diluted in the cream prepared beforehand.

To obtain a cream containing 0.01% active principle, 36% of the solution of lipid nanocapsules according to Example 2 was diluted in the emulsion.

To obtain a cream containing 0.003% active principle, 9% of the solution of lipid nanocapsules according to Example 2 was diluted in the cream.

| Ingredients | Compositions (% m/m) | |
|---|---|---|
| | No. 16 | No. 17 |
| Compound A | 0.01 | 0.003 |
| Diisopropyl adipate (Crodamol DA) | 4.96 | 1.24 |
| Hydrogenated phosphatidylcholine (Phospholipon 90H) | 0.72 | 0.18 |
| Decamethylcyclopentasiloxane (ST-Cyclomethicone 5NF) | 13.0 | 13.0 |
| Perhydrosqualene | 6.0 | 6.0 |
| Glucamate SSE 20 | 3.5 | 3.5 |
| Glucate SS | 3.5 | 3.5 |
| Glycerol | 3.0 | 3.0 |
| Propylene Glycol | 4.0 | 4.0 |
| Carbomer (Carbopol Ultrez 20) | 0.40 | 0.40 |
| Methyl paraben | 0.20 | 0.20 |
| Propyl paraben | 0.10 | 0.10 |
| EDTA | 0.10 | 0.10 |
| Triethanolamine | qs pH 5.5 ± 0.5 | qs pH 5.5 ± 0.5 |
| Purified water | qs 100 | qs 100 |

EXAMPLE 10

Examples of Compositions of Lotion Type According to the Invention Containing Compound A

| Ingredients | Compositions (% m/m) | |
|---|---|---|
| | No. 18 | No. 19 |
| Compound A | 0.01 | 0.003 |
| Diisopropyl adipate (Crodamol DA) | 4.96 | 1.24 |
| Hydrogenated phosphatidylcholine (Phospholipon 90H) | 0.72 | 0.18 |
| Perhydrosqualene | 5.0 | 5.0 |
| Cetostearyl isononanoate | 5.0 | 5.0 |
| Steareth-21 (Brij 721) | 3.0 | 3.0 |
| Glyceryl stearate and PEG-100 stearate (Arlacel 165FL) | 3.0 | 3.0 |
| Dipropylene glycol | 3.0 | 3.0 |
| Acrylamide, AMPS Copolymer Dispersion 40%/Isohexadecane (Simulgel 600 PHA) | 1.40 | 1.40 |
| Methyl paraben | 0.15 | 0.15 |
| Propyl paraben | 0.10 | 0.10 |
| Triethanolamine | qs pH 5.5 ± 0.5 | qs pH 5.5 ± 0.5 |
| Purified water | qs 100 | qs 100 |

EXAMPLE 11

Tolerance Study: Evaluation of the Pro-inflammatory Effect of the Formulations after a Single Application to the Ear of BALB/C Mice The aim of the study is to evaluate the effect of a composition according to the invention on the pro-inflammatory activity associated with retinoids in general.

A single application of 20 μl of the test products was administered to the ear of the mice on day 1. Clinical observations and measurements of the mouse ear thickness, directly linked to inflammation, are performed from day 2 up to day 12.

It was observed that compound A in a single topical application, at 0.01% in acetone, induced a significant inflammatory effect, with an increase in the thickness of the mouse ear of 59% versus acetone alone.

On the other hand, when incorporated to 0.01% into the gel composition 1 of Example 3, the single topical application of compound A induces a moderate inflammation of 40%, i.e. a significant 32% reduction in inflammation.

EXAMPLE 12

Study of Cutaneous Tolerance in the Göttingen Pig Model

The object of this study is to evaluate the tolerance of the gel composition 1 of Example 3 by repeated application using the Göttingen pig tolerance model compared with a reference formulation of compound A in which the active agent is dissolved and not encapsulated in a reference aqueous-alcoholic gel. The two formulations are evaluated at the same concentration of 0.01%.

50 μl of each formulation are applied to the animal's back for 4 weeks, and each application is repeated six times. The cutaneous reactions of erythema and edema type are evaluated every week after 7 days of application, on an index scale ranging from 0 to 5.0.

The results are as follows:

|  | Mean weekly indices | | | |
| --- | --- | --- | --- | --- |
|  | Week 1 | Week 2 | Week 3 | Week 4 |
| Reference formulation | 0.000 | 0.071 | 0.238 | 0.875 |
| Composition 1 of Example 3 | 0.000 | 0.000 | 0.000 | 0.146 |

After 4 weeks of application, it was observed that composition 1 of Example 3 is 6 times less irritant than the reference formulation in which compound A is dissolved but not encapsulated.

EXAMPLE 13

Study of Comedolytic Activity

The comedolytic activity of composition 2 of Example 3 was analyzed by measuring the reduction in the number of comedones, after topical application to the back of Rhino mice everyday for 11 days versus placebo.

50 μl of composition 2 of Example 2 containing 0.003% of compound A are applied.

After 11 days of application, a significant 70% reduction in the number of comedones is observed with the composition according to the invention, versus 2% for the placebo.

This study thus demonstrates the activity of the composition according to the invention for treating acne. The established efficacy of the composition according to the invention demonstrates that, despite the internalization of the active agent in the nanocapsule, it was indeed released and penetrated into the skin to exert its activity therein, while at the same time being better tolerated.

The invention claimed is:

1. A composition comprising a nanodispersion in a pharmaceutically acceptable vehicle, the nanodispersion comprising lipid nanocapsules dispersed in a hydrophilic phase, wherein the lipid nanocapsules comprise:
   an oily inner phase and a non-polymeric envelope obtained from at least one surfactant chosen from amphiphilic lipids, wherein the oily inner phase consists of a fatty substance that is liquid or semiliquid at room temperature and at least one retinoid as an irritant active principle dissolved in the fatty substance, wherein the nanocapsule does not comprise any organic solvent of alcoholic type, wherein the surfactant is a lecithin with a weight amount of hydrogenated phosphatidylcholine of greater than 85%, wherein the fatty substance comprises at least one oily solvent, and wherein the ratio of the inner oily phase to the amount of lecithin is from 5/1 to 7/1; and
   wherein the composition comprises, on a weight basis relative to the total weight of the composition,
   0.01% to 10% of the surfactant,
   0.1% to 50% of the fatty substance, and
   0.00001% to 0.3% of at least 3"-tert-butyl-4'-(2-hydroxyethoxy)-4"-pyrrolidin-1-yl[1,1';3',1"]-terphenyl-4-carboxylic acid as the retinoid.

2. The composition as claimed in claim 1, wherein the surfactant has a transition temperature of greater than 35° C.

3. The composition as claimed in claim 1, wherein the surfactant has a transition temperature of greater than 45° C.

4. The composition as claimed in claim 1, wherein the nanocapsule is free of co-surfactant other than the phospholipids.

5. The composition as claimed in claim 1, wherein the nanocapsule is free of polymer.

6. The composition as claimed in claim 1, wherein the fatty substance is liquid at room temperature.

7. The composition as claimed in claim 1, wherein the at least one oily solvent is selected from the group consisting of polyethoxylated fatty acids, triglycerides and oils comprising the same, and fatty acid esters.

8. The composition as claimed in claim 1, wherein the oily inner phase is a fatty acid ester.

9. The composition as claimed in claim 6, wherein the oily inner phase is diisopropyl adipate.

10. The composition as claimed in claim 1, wherein the oily inner phase is present in an amount of from 50% to 99.997% by weight relative to the total weight of the inner phase.

11. The composition as claimed in claim 1, wherein the nanocapsule has a mean size of less than 900 nm.

12. The composition as claimed in claim 11, wherein the nanocapsule has a mean size of less than 500 nm.

13. The composition as claimed in claim 1, wherein the composition improves the tolerance of the irritant active principle.

14. The composition as claimed in claim 1, wherein the pharmaceutically acceptable vehicle is a gel.

15. The composition as claimed in claim 1, wherein the pharmaceutically acceptable vehicle is a solution.

16. The composition as claimed in claim 1, wherein the pharmaceutically acceptable vehicle is an oil-in-water emulsion.

17. The composition as claimed in claim 1, wherein the composition comprises, in a pharmaceutically acceptable vehicle, on a weight basis relative to the total weight of the composition:
   0.1% to 5% of lecithin; and
   1% to 5% of fatty acid esters.

18. The composition as claimed in claim 1, wherein the composition is in a form suitable for topical administration.

19. The composition as claimed in claim 1, wherein the composition is in the form of a medicament.

20. A method of treating a dermatological complaint selected from the group consisting of keratinization disorders, conditions associated with keratinization disorders; dermatological conditions with an inflammatory immunoallergic component; conditions caused by exposure to UV radiation, skin aging, actinic keratosis, or chronological or actinic aging; conditions associated with benign dermal or epidermal proliferations; immune dermatoses; cutaneous or mucosal cancerous or precancerous conditions; stigmata of epidermal and/or dermal atrophy induced by local or systemic corticosteroids; cutaneous atrophy; healing disorders; conditions of fungal origin at the cutaneous level; and pigmentation disorders, the method comprising administering to an individual subject in need thereof an effective amount of the composition as defined in claim 1.

21. The method as defined in claim 20, wherein the dermatological complaint is selected from the group consisting of acne, ichthyosis, ichthyosiform conditions, palmoplantar hyperkeratosis and psoriasis.

22. A process for preparing a composition as claimed in claim 1, wherein the process comprises the following steps:
   (i) dissolving the irritant active principle in a fatty substance that is liquid or semiliquid at room temperature, to obtain the oily phase;
   (ii) preparing the hydrophilic phase;
   (iii) dispersing the lipophilic surfactant in the oily phase obtained in (i) or in the hydrophilic phase obtained in (ii);
   (iv) heating the oily and hydrophilic phases separately to about 75° C.;
   (v) mixing with stirring the oily and hydrophilic phases obtained after step (iv);
   (vi) introducing the mixture obtained in (v) into a high-pressure homogenizer to obtain a composition of lipid nanocapsules; and
   (vii) incorporating the preceding composition into a pharmaceutically acceptable vehicle.

23. The composition as claimed in claim 1, wherein the surfactant is present in an amount of 0.05% to 5% by weight.

24. The composition as claimed in claim 1, wherein the surfactant is present in an amount from 0.1% to 1% by weight.

25. The composition as claimed in claim 1, wherein the ratio of the inner oily phase to the amount of lecithin is from 6/1 to 7/1.

26. The composition as claimed in claim 1, wherein a particle size of the nanocapsule remains stable after 3 months relative to the particle size of the nanocapsule at an initial time.

27. The composition as claimed in claim 1, wherein the nanocapsule is chemically stable for at least 6 months.

* * * * *